US011687152B1

(12) United States Patent
Mene et al.

(10) Patent No.: US 11,687,152 B1
(45) Date of Patent: Jun. 27, 2023

(54) DIRECTIONAL RECOMMENDATIONS BASED ON MOVEMENT TRACKING WHILE PERFORMING AN ACTIVITY

(71) Applicant: International Business Machines Corporation, Armonk, NY (US)

(72) Inventors: Atul Mene, Morrisville, NC (US); Jeremy R. Fox, Georgetown, TX (US); Tushar Agrawal, West Fargo, ND (US); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/930,490

(22) Filed: Sep. 8, 2022

(51) Int. Cl.
| | | |
|---|---|---|
| *G01G 19/03* | (2006.01) | |
| *G06F 3/01* | (2006.01) | |
| *A61B 5/11* | (2006.01) | |
| *G06N 3/08* | (2023.01) | |
| *G16Y 40/10* | (2020.01) | |

(52) U.S. Cl.
CPC ............ *G06F 3/011* (2013.01); *A61B 5/1118* (2013.01); *G06N 3/08* (2013.01); *G16Y 40/10* (2020.01)

(58) Field of Classification Search
CPC ......... G06F 3/011; A61B 5/1118; G06N 3/08; G16Y 40/10
USPC ................................ 702/175, 153; 345/156
See application file for complete search history.

(56) References Cited

U.S. PATENT DOCUMENTS

| | | |
|---|---|---|
| 9,256,785 B2 | 2/2016 | Qvarfordt |
| 9,350,951 B1 | 5/2016 | Rowe |
| 9,495,383 B2 | 11/2016 | Mishra |
| | (Continued) | |

FOREIGN PATENT DOCUMENTS

WO   2015139089 A1   9/2015

OTHER PUBLICATIONS

Authors et. al.: Disclosed Anonymously, "A method to intelligently optimize user interface based on Generative Adversarial Networks", An IP.com Prior Art Database Technical Disclosure, IP.com No. IPCOM000262277D, IP.com Electronic Publication Date: May 16, 2020, 4 pages.

(Continued)

*Primary Examiner* — Thuy N Pardo
(74) *Attorney, Agent, or Firm* — Erika R. DeCosty

(57) ABSTRACT

A computer-implemented method is disclosed which includes determining a current activity of an individual, comparing movements of the individual while performing the current activity to corresponding movements in a reference activity, determining whether a performance level of respective movements of the individual while performing the current activity are within a predetermined performance range for corresponding movements in the reference activity, generating, via a generative adversarial network (GAN), a directional guidance recommendation based, at least in part, on: a comparative analysis of the movement of the individual while performing the current activity and the corresponding movement included in the reference activity, and a degree of deviation between the performance level of the at least one movement of the individual and an optimal performance level of the corresponding movement included in the reference activity, and displaying the generated directional guidance recommendation to the individual.

20 Claims, 6 Drawing Sheets

(56) References Cited

U.S. PATENT DOCUMENTS

| | | | |
|---|---|---|---|
| 2008/0086236 A1* | 4/2008 | Saito | G05D 1/0251 901/1 |
| 2010/0045469 A1* | 2/2010 | Reijndorp | G06F 3/011 340/573.7 |
| 2011/0010129 A1* | 1/2011 | Kirby | G01B 11/002 702/153 |
| 2011/0270135 A1 | 11/2011 | Dooley | |
| 2015/0122018 A1* | 5/2015 | Yuen | A61B 5/4812 73/514.01 |
| 2015/0179040 A1* | 6/2015 | Nishihara | H04W 4/026 340/539.12 |
| 2018/0012241 A1* | 1/2018 | Jones | G01V 3/12 |
| 2018/0121728 A1 | 5/2018 | Wells | |
| 2018/0211563 A1* | 7/2018 | Savitsky | G09B 9/00 |
| 2018/0314992 A1 | 11/2018 | Flinn | |
| 2019/0030394 A1 | 1/2019 | Orr | |
| 2019/0183412 A1* | 6/2019 | Huijbregts | A61B 5/165 |
| 2019/0192141 A1* | 6/2019 | Shelton, IV | A61B 46/10 |
| 2020/0365044 A1 | 11/2020 | Trim | |
| 2021/0048879 A1 | 2/2021 | Trim | |
| 2021/0110614 A1* | 4/2021 | Shahrokni | G06T 7/73 |
| 2021/0241878 A1* | 8/2021 | Karunanithi | A61B 5/7282 |
| 2021/0294809 A1* | 9/2021 | Helvik | G06F 16/38 |
| 2021/0406449 A1* | 12/2021 | Meling | G06F 40/166 |
| 2022/0035443 A1* | 2/2022 | Winold | G16H 40/63 |
| 2022/0222279 A1* | 7/2022 | Kohlmeier | G06F 16/9035 |
| 2022/0284031 A1* | 9/2022 | Helvik | G06F 16/951 |
| 2022/0353307 A1* | 11/2022 | Wang | G06N 20/00 |

OTHER PUBLICATIONS

Authors et. al.: Disclosed Anonymously, "Sport Movement Correction and Skill Improvement by Mobile Device with Augmented Reality", An IP.com Prior Art Database Technical Disclosure, IP.com No. IPCOM000269316D, Ip.com Electronic Publication Date: Apr. 2, 2022, 3 pages.

Authors et. al.: Disclosed Anonymously, "Virtual Reality-Based System for Controlling Required Position of Patient for Medical Treatment", An IP.com Prior Art Database Technical Disclosure, IP.com No. IPCOM000264795D, IP.com Electronic Publication Date: Jan. 27, 2021, 5 pages.

Brownlee, Jason, "A Gentle Introduction to Generative Adversarial Networks (GANs)", on Jun. 17, 2019 in Generative Adversarial Networks, Last Updated on Jul. 19, 2019, 36 pages.

Lei, Nin, "Generative Adversarial Network technology: AI goes mainstream", Sep. 17, 2019, 5 pages, <https://www.ibm.com/blogs/systems/generative-adversarial-network-technology-ai-goes-mainstream/>.

Mell et al., "The NIST Definition of Cloud Computing", Recommendations of the National Institute of Standards and Technology, Special Publication 800-145, Sep. 2011, 7 pages.

Saleem, Huzaifah, "What is generative AI and how much power does it have", Published Aug. 20, 2020, IBM Developer Blog Post, 6 pages, <https://developer.ibm.com/blogs/what-is-generative-ai-and-how-much-power-does-it-have/>.

* cited by examiner

DIRECTIONAL RECOMMENDATIONS BASED ON MOVEMENT TRACKING WHILE PERFORMING AN ACTIVITY

BACKGROUND

The present invention relates generally to the field of tracking movements while performing an activity, and more particularly to, providing directional recommendations based on the movements tracked while performing the activity.

An IoT enabled system can include A wearable device, head mounted augmented reality (AR) glasses, cap, electronic cloth based dress, shoes etc. IoT enabled devices generate information when any criteria or condition for an activity is met. An IoT enabled system can track what activity is being performed and how the activity is performed. For example, arranging books on shelf, jogging, or organizing objects. While using any IoT enabled system, the sensors installed on those devices will be capturing different types of data from the activity and can identify the sequence of the steps within a given activity.

SUMMARY

According to one embodiment of the present invention, a computer-implemented method is disclosed. The computer-implemented method includes determining a current activity of an individual. The computer-implemented method further includes comparing movements of the individual while performing the current activity to corresponding movements in a reference activity. The computer-implemented method further includes determining whether a performance level of respective movements of the individual while performing the current activity are within a predetermined performance range associated with the corresponding movements in the reference activity. The computer-implemented method further includes responsive to determining that the performance level of at least one movement of the individual while performing the current activity is outside of the predetermined performance range of a corresponding movement included in the reference activity, generating, via a generative adversarial network (GAN), a directional guidance recommendation based, at least in part, on: a comparative analysis of the at least one movement of the individual while performing the current activity and the corresponding movement included in the reference activity, and a degree of deviation between the performance level of the at least one movement of the individual and an optimal performance level of the corresponding movement included in the reference activity. The computer-implemented method further includes displaying the generated directional guidance recommendation to the individual while the individual is performing the current activity.

According to another embodiment of the present invention, a computer program product is disclosed. The computer program product includes one or more computer readable storage media and program instructions stored on the one or more computer readable storage media. The program instructions include instructions to determine a current activity of an individual. The program instructions further include instructions to compare movements of the individual while performing the current activity to movements associated with a reference activity. The program instructions further include instructions to determine whether a performance level of respective movements of the individual while performing the current activity are within a predetermined performance range associated with corresponding movements in the reference activity. The program instructions further include instructions to responsive to determining that the performance level of at least one movement of the individual while performing the current activity is outside of the predetermined performance range of a corresponding movement included in the reference activity, generate, via a generative adversarial network (GAN), a directional guidance recommendation based, at least in part, on: a comparative analysis of the at least one movement of the individual while performing the current activity and the corresponding movement included in the reference activity, and a degree of deviation between the performance level of the at least one movement of the individual and an optimal performance level of the corresponding movement included in the reference activity. The program instructions further include instructions to display the generated directional guidance recommendation to the individual while the individual is performing the current activity.

According to another embodiment of the present invention, a computer system is disclosed. The computer system includes one or more computer processors, one or more computer readable storage media, and computer program instructions, the computer program instructions being stored on the one or more computer readable storage media for execution by the one or more computer processors. The program instructions include instructions to determine a current activity of an individual. The program instructions further include instructions to compare movements of the individual while performing the current activity to movements associated with a reference activity. The program instructions further include instructions to determine whether a performance level of respective movements of the individual while performing the current activity are within a predetermined performance range associated with corresponding movements in the reference activity. The program instructions further include instructions to responsive to determining that the performance level of at least one movement of the individual while performing the current activity is outside of the predetermined performance range of a corresponding movement included in the reference activity, generate, via a generative adversarial network (GAN), a directional guidance recommendation based, at least in part, on: a comparative analysis of the at least one movement of the individual while performing the current activity and the corresponding movement included in the reference activity, and a degree of deviation between the performance level of the at least one movement of the individual and an optimal performance level of the corresponding movement included in the reference activity. The program instructions further include instructions to display the generated directional guidance recommendation to the individual while the individual is performing the current activity.

BRIEF DESCRIPTION OF DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
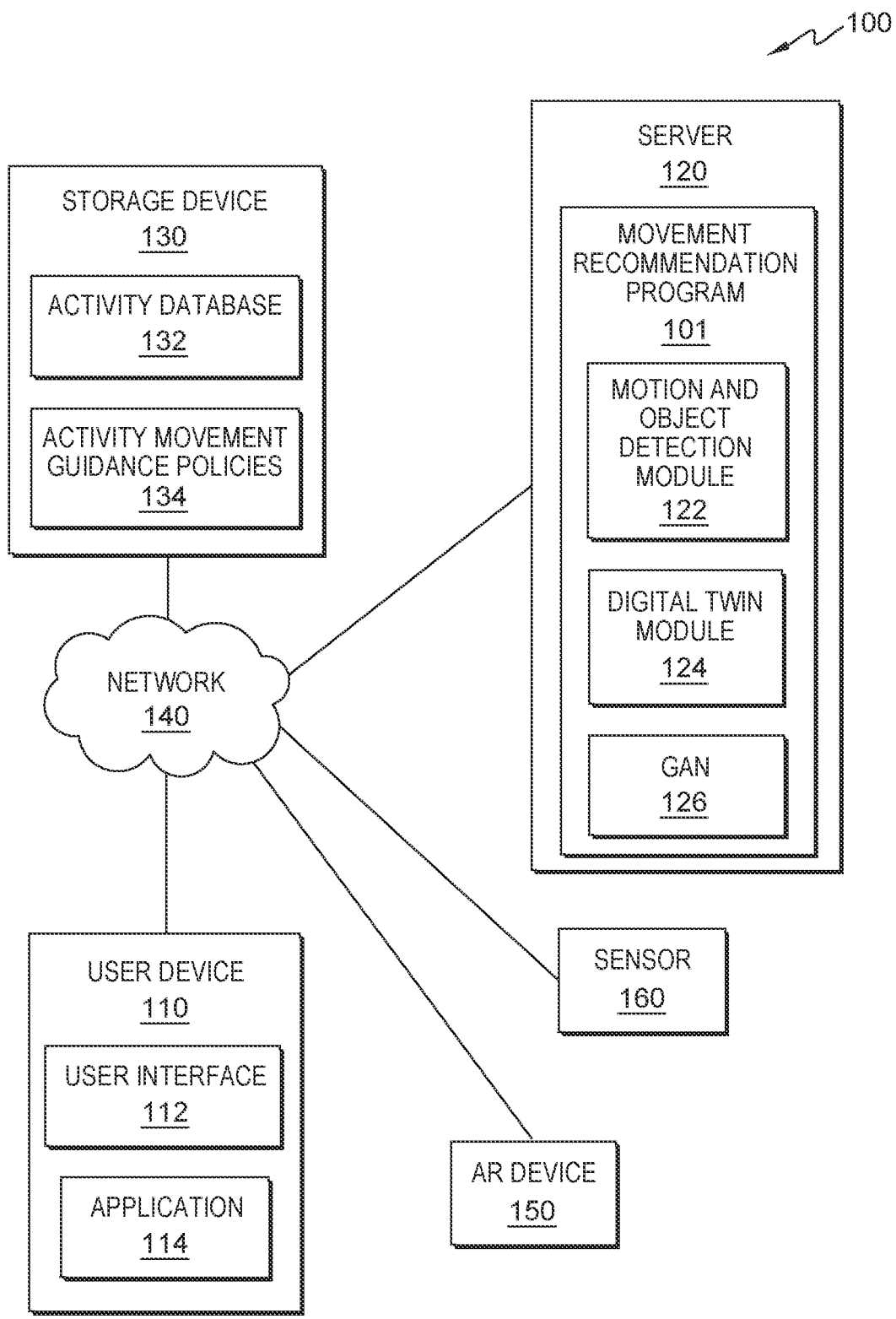
FIG. 1 is a block diagram of a network computing environment for movement recommendation program 101, generally designated 100, in accordance with at least one embodiment of the present invention.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

The present invention relates generally to the field of tracking movements while performing an activity, and more particularly to, providing directional recommendations based on the movements tracked while performing the activity.

In many instances, it is desirable to perform a certain activity in a precise way. For example, handing a delicate item may require a user to hold the delicate item in a certain way, by a certain angle, or force to ensure not to drop or break the item. Activities with multiple steps may require the user to perform the steps in a particular order or way in order to achieve desired results. For example, displaying new clothes for a store can consist of unboxing the clothes, steaming the clothes, and folding or hanging up the clothes. Further, certain similar activities may be required to be performed multiple times. For example, folding clothes for a store which are to be folded in a particular consistent manner. However, it can be difficult to achieve consistent results between different users or a singular user multiple times. For example, it may be difficult for two users to fold a shirt the same way or for one user to fold a shirt the same way every time.

While performing various activities, a user can one or more IoT enabled devices that generate signals that enable the continuous tracking of how the activity is performed. For example, robotic arms can generate IoT signals while performing a particular activity. In this case, if any activity is to be executed in a same manner on how it was done before or by another person or by robotic system, then we need to compare the IoT signals of previous activity with the correct activity in order to guide the current activity being performed.

Embodiments of the present invention monitor a user performing an activity. Embodiments of the present invention determine the activity the user is performing. For example, the present invention determines the user is assembling a chair. Embodiments of the present invention determine the preferred steps and motion for the activity. For example, embodiments of the present invention determine the preferred steps and hand motions for assembling a chair. Embodiments of the present invention determine an amount or percent of deviation from the users steps and motions of performing an activity from the preferred steps and motions for performing an activity. Embodiments of the present invention determine one or more recommendation directions for a given activity. For example, embodiments of the present invention determine a recommendation to have the user move their hand up higher to assemble the chair. Embodiments of the present invention utilize a generative adversarial network (GAN) to generate direction recommendations to the user. Embodiments of the present invention display one or more graphical, pictorial, audio, or word directional recommendations to the user. For example, embodiments of the present invention display a looping image of a person raising their hand to recommend to the user to raise their hand higher during a particular assembly step of the chair.

For example, assume that as new team members have joined a team, the new team members are asked to perform the activity in the same way how any previous activity was performed by a previous team member, or how the activity is supposed to be performed. Embodiments of the present invention recognize the need for a system to show how the activities are to be performed and how they were performed in the past in order to maintain contain consistency while performing a particular activity. Embodiments of the present invention further recognize the need for a system to recommend directional movements to perform the activity in the same steps or using similar movements to how the previous activity was performed.

In embodiments of the present invention, the user can specify any reference historical activity which is to be aligned with the current activity, and accordingly based on the reference activity, the user will start getting appropriate notifications if the current activity being performed is not aligned (deviates by a particular activity metric threshold) with the reference activity. For example, the user specifies the reference historical activity to be aligned with the current activity of restocking items on a shelf and the user receives a notification when their movement of restocking the items on the shelf is not aligned with the movement of the reference historical activity of restocking items on a shelf. In an embodiment, the determination of movement for an activity not being aligned with the movement of the reference historical activity is based, at least in part, on a predetermined performance activity threshold.

Embodiments of the present invention identify individual steps from the activity. In an embodiment, the user can reference multiple historical activities to perform a single activity. Embodiments of the present invention determine different steps of the current activity to be referenced with respective steps of one or more similar historical activities. Accordingly, the user can get appropriate notifications if any step of the activity is not aligned with respective steps of one or more historically referenced activity steps.

Embodiments of the present invention determine a level of deviation from a projected AR directional guidance for one or more steps associated with a particular activity. Embodiments of the present invention compare the steps of the activity with historical activity data or historical activity steps. Embodiments of the present invention compare the movement from the current activity and historically captured movement of the one or more historically referenced activities. Embodiments of the present invention identify an appropriate range of deviation and movement recommendations for the user. Embodiments of the present invention notify the user of the one or more movement recommendations. For example, embodiments of the present invention display a visualization of a user moving their arm downwards in an AR field of view of the user to recommend the user to move their arm downwards.

Embodiments of the present invention determine the degree of deviation via digital twin comparison. Embodiments of the present invention compare the degree of deviation of the IoT signals from a current activity and the historically referenced activity via digital twin simulation. Embodiments of the present invention recommend how the current activity can be aligned with the historically performed activity and appropriate alerts will be provided to the user if a performance metric associated with the activity deviates above a predetermined threshold from the historically referenced activity.

Embodiments of the present invention determine generative adversarial network (GAN) infusion for pictorial machine learning. Embodiments of the present invention utilize a GAN and IoT signals from various IoT devices for the historically referenced activity to create a sequence of images. Embodiments of the present invention generate appropriate visualization of the historically referenced activity to be shown in the AR field of view of the user.

Embodiments of the present invention include a feedback loop for improvement. In embodiments of the present invention which include a robotic system, the user can reference multiple automatic and/or manually performed activities, and accordingly the robotic system will aggregate the IoT signals from the referenced activities as the current activity is executed.

The present invention may be a system, a method, and/or a computer program product at any possible technical detail level of integration. The computer program product may include a computer readable storage medium (or media) having computer readable program instructions thereon for causing a processor to carry out aspects of the present.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suit-able combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention will now be described in detail with reference to the Figures. FIG. 1 is a functional block diagram of a network computing environment for movement recommendation program 101, generally designated 100, in accordance with at least one embodiment of the present invention. In an embodiment, network computing environment 100 may be provided by cloud computing environment 50, as depicted and described with reference to FIG. 5, in accordance with at least one embodiment of the present invention. FIG. 1 provides an illustration of only one implementation and does not imply any limitations with regard to the environments in which different embodiments may be implemented. Many modifications to the depicted environment may be made by those skilled in the art without departing from the scope of the present invention as recited by the claims.

Network computing environment 100 includes user device 110, server 120, storage device 130, AR device 150, and sensor 160, interconnected over network 140. User device 110 may represent a computing device of a user, such as a laptop computer, a tablet computer, a netbook computer, a personal computer, a desktop computer, a personal digital assistant (PDA), a smart phone, a wearable device (e.g., smart glasses, smart watches, e-textiles, AR headsets, etc.), or any programmable computer systems known in the art. In general, user device 110 can represent any programmable electronic device or combination of programmable electronic devices capable of executing machine readable program instructions and communicating with server 120, storage device 130 and other devices (not depicted) via a network, such as network 140. User device 110 can include internal and external hardware components, as depicted, and described in further detail with respect to FIG. 4.

User device 110 further includes user interface 112 and application 114. User interface 112 is a program that provides an interface between a user of an end user device, such as user device 110, and a plurality of applications that reside on the device (e.g., application 114). A user interface, such as user interface 112, refers to the information (such as graphic, text, and sound) that a program presents to a user, and the control sequences the user employs to control the program. A variety of types of user interfaces exist. In one embodiment, user interface 112 is a graphical user interface. A graphical user interface (GUI) is a type of user interface that allows users to interact with electronic devices, such as a computer keyboard and mouse, through graphical icons and visual indicators, such as secondary notation, as opposed to text-based interfaces, typed command labels, or text navigation. In computing, GUIs were introduced in reaction to the perceived steep learning curve of command-line interfaces which require commands to be typed on the keyboard. The actions in GUIs are often performed through direct manipulation of the graphical elements. In another embodiment, user interface 112 is a script or application programming interface (API).

Application 114 can be representative of one or more applications (e.g., an application suite) that operate on user device 110. In an embodiment, application 114 is representative of one or more applications (e.g., task applications, video streaming applications, augmented reality applications) located on user device 110. In various example embodiments, application 114 can be an application that a user of user device 110 utilizes to visualize an activity or list of tasks or steps for a particular activity or directional recommendations for completing the activity. In an embodiment, application 114 can be a client-side application associated with a server-side application running on server 120 (e.g., a client-side application associated with movement recommendation program 101). In an embodiment, application 114 can operate to perform processing steps of movement recommendation program 101 (i.e., application 114 can be representative of movement recommendation program 101 operating on user device 110).

Server 120 is configured to provide resources to various computing devices, such as user device 110. For example, server 120 may host various resources, such as movement recommendation program 101, motion and object detection module 122, digital twin module 124, and GAN 126, that are accessed and utilized by a plurality of devices. In various embodiments, server 120 is a computing device that can be a standalone device, a management server, a web server, an application server, a mobile device, or any other electronic device or computing system capable of receiving, sending, and processing data. In an embodiment, server 120 represents a server computing system utilizing multiple computers as a server system, such as in a cloud computing environment. In an embodiment, server 120 represents a computing system utilizing clustered computers and components (e.g. database server computer, application server computer, web server computer, webmail server computer, media server computer, etc.) that act as a single pool of seamless resources when accessed within network computing environment 100. In general, server 120 represents any programmable electronic device or combination of programmable electronic devices capable of executing machine readable program instructions and communicating with each other, as well as with user device 110, storage device 130, and other computing devices (not shown) within network computing environment 100 via a network, such as network 140.

Figure 4:
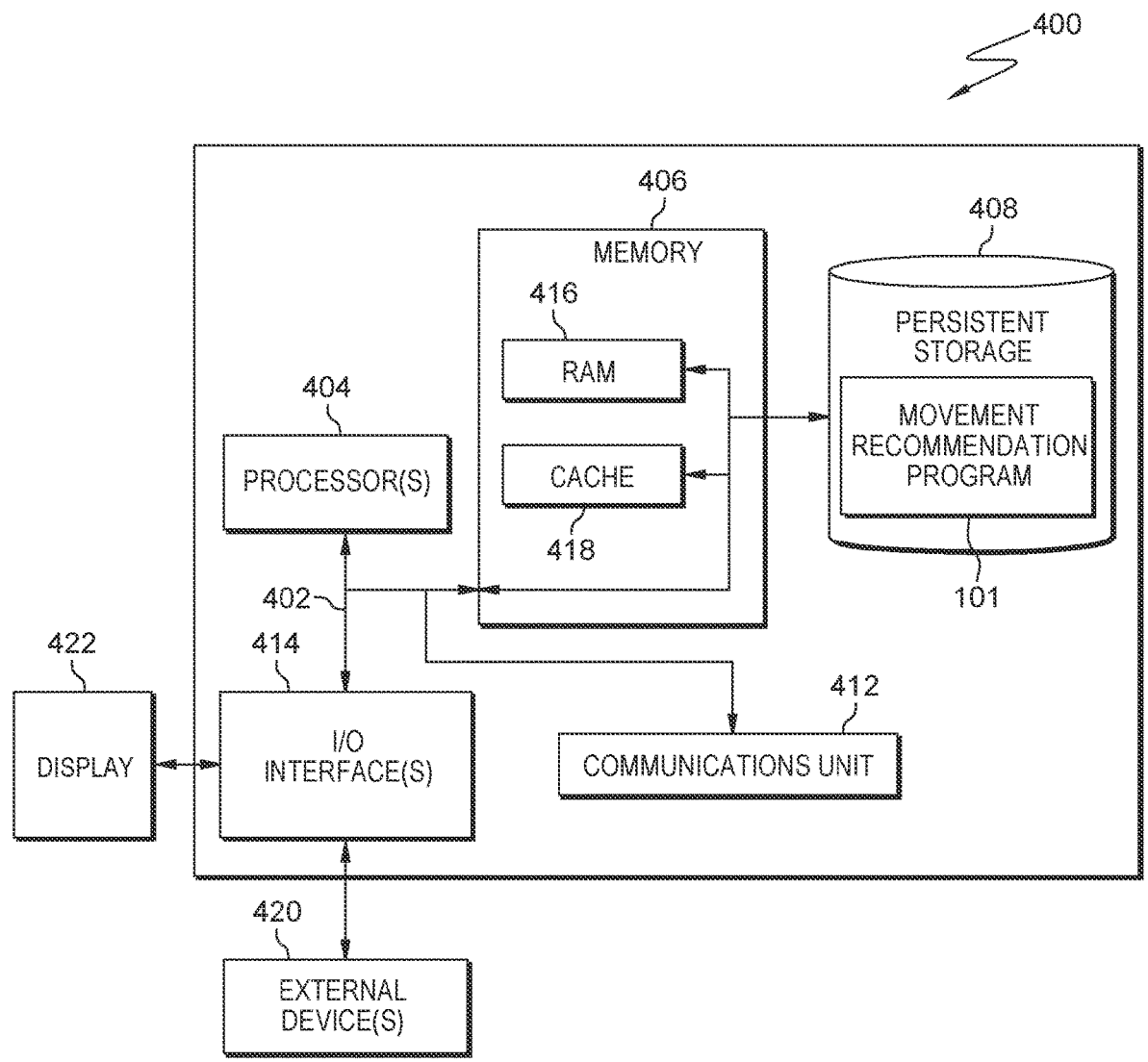
FIG. 4 is a block diagram depicting components of a computer, generally designated 400, suitable for executing a movement recommendation program 101 in accordance with at least one embodiment of the present invention.
Figure 5:
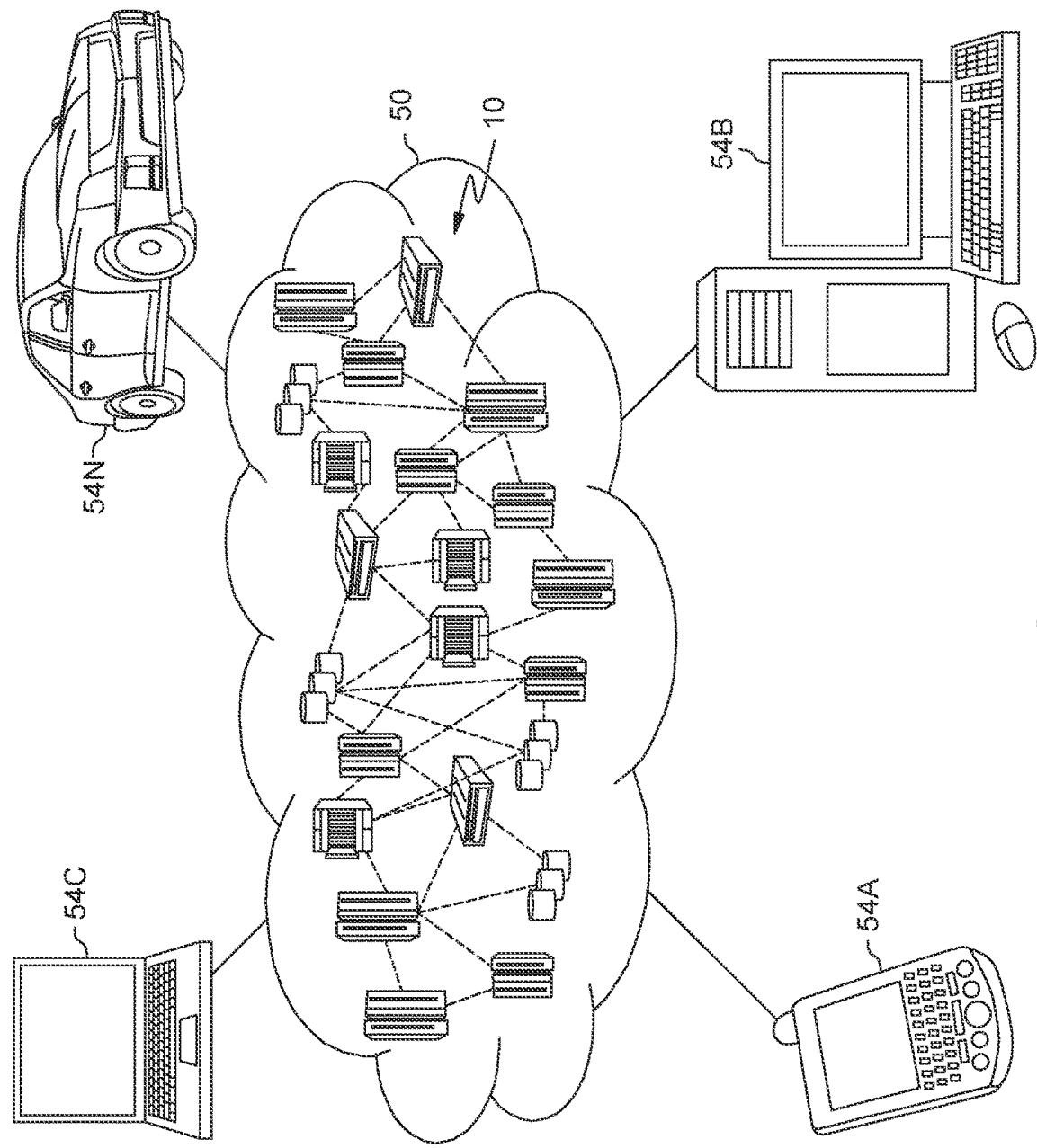
FIG. 5 is a block diagram depicting a cloud computing environment 50 in accordance with at least one embodiment of the present invention.

Server 120 may include components as depicted and described in detail with respect to cloud computing node 10, as described in reference to FIG. 5, in accordance with at least one embodiment of the present invention. Server 120 may include components, as depicted and described in detail with respect to computing device 400 of FIG. 4, in accordance with at least one embodiment of the present invention.

In an embodiment, server 120 includes movement recommendation program 101, which further includes motion and object detection module 122, digital twin module 124, and GAN 126. In an embodiment, movement recommendation program 101 may be configured to access various data sources, such as storage device 130, activity database 132, and activity movement guidance policies 134 that may include personal data, content, contextual data, or information that a user does not want to be processed. Personal data includes personally identifying information or sensitive personal information as well as user information, such as location tracking or geolocation information. Processing refers to any operation, automated or unautomated, or set of operations such as collecting, recording, organizing, structuring, storing, adapting, altering, retrieving, consulting, using, disclosing by transmission, dissemination, or otherwise making available, combining, restricting, erasing, or destroying personal data. In an embodiment, movement recommendation program 101 enables the authorized and secure processing of personal data. In an embodiment, movement recommendation program 101 provides informed consent, with notice of the collection of personal data, allowing the user to opt in or opt out of processing personal data. Consent can take several forms. Opt-in consent can impose on the user to take an affirmative action before personal data is processed. Alternatively, opt-out consent can impose on the user to take an affirmative action to prevent the processing of personal data before personal data is processed. In an embodiment, movement recommendation program 101 provides information regarding personal data and the nature (e.g., type, scope, purpose, duration, etc.) of the processing. In an embodiment, movement recommendation program 101 provides a user with copies of stored personal data. In an embodiment, movement recommendation program 101 allows for the correction or completion of incorrect or incomplete personal data. In an embodiment, movement recommendation program 101 allows for the immediate deletion of personal data.

In an embodiment, movement recommendation program 101 requests the user to opt-in to obtaining, recording, and storing their personal data. In an embodiment, movement recommendation program 101 obtains, records, and stores, user information from AR device 150 or sensor 160. For example, movement recommendation program 101 receives information on users height from AR device 150 or sensor 160 based, at least in part, on the users field of view. In an embodiment, movement recommendation program 101 receives information from AR device 150 or sensor 160 while performing any activity and the user can allow the IoT signals to record for the activity is being performed.

In an embodiment, motion and object detection module 122 is a computer algorithm used to determine the motion, distance, and type of object within a field of view or augmented reality field of view of a person. For example, motion and object detection module 122 determines there is table 5 feet in front of the user and the user is reaching their left arm out in front of them. In an embodiment, motion and object detection module 122 detects moving objects within a field of view or augmented reality field of view of a person. In an embodiment, a convolutional neural network based method (e.g., YOLOx3-SOD) is employed to detect all objects in an image or field of view of a person, by fusing the results obtained by motion detection and object detection.

In an embodiment, digital twin module 124 is a computer algorithm used to generate a virtual model designed to accurately reflect a physical object. In an embodiment, the virtual representation of an object or system that spans its lifecycle, is updated from real-time data, and uses simulation, machine learning and reasoning to help decision-making. For example, movement recommendation program 101 receives information on the movement of a user performing the activity of planting a garden. This data is then applied to digital twin module 124 to generate a digital twin simulation of the corrected movement of a user performing the activity of planting a garden. For example, movement recommendation program 101 determines the user should space the plants farther apart, the digital twin simulation depicts the user digging the holes for each plant farther apart.

In an embodiment, GAN 126 is a pair of neural networks that, given a training set, compete within one another to generate new data with the same characteristics as the training set. In an embodiment, GAN 126 is utilized to regenerate one or more objects or guidance recommendations. In an embodiment, GAN 126 is trained using previously identified activities and steps from the reference activity. For example, GAN 126 is trained using a previously identified activity of user A planting flowers. In an embodiment, GAN 126 is trained to identify one or more steps in an activity. For example, the activity of planting flowers includes one step of filling a pot partially with soil and a second step of placing a plant in the pot.

In various embodiments, storage device 130 is a secure data repository for persistently storing activity database 132 and activity movement guidance policies 134 utilized by various applications and user devices of a user, such as user device 110. Storage device 130 may be implemented using any volatile or non-volatile storage media known in the art for storing data. For example, storage device 130 may be implemented with a tape library, optical library, one or more independent hard disk drives, multiple hard disk drives in a redundant array of independent disks (RAID), solid-state drives (SSD), random-access memory (RAM), and any possible combination thereof. Similarly, storage device 130 may be implemented with any suitable storage architecture known in the art, such as a relational database, an object-oriented database, or one or more tables.

In an embodiment activity database 132 comprises information relating to activities, steps, and users. In an embodiment, activity database 132 includes information on the directional motions a user does to perform an activity. For example, activity database 132 includes information on the movements that user A needs to perform to complete the activity of building a shelf. In an embodiment, movement recommendation program 101 creates a knowledge corpus, such as activity database 132, for each activity. In an embodiment, movement recommendation program 101 determines future activities based, at least in part, on the stored information in activity database 132. In an embodiment, movement recommendation program 101 stores the determined activity and the same will be stored in the knowledge corpus. In an embodiment, movement recommendation program 101 determines the activity can be performed with robotic system, and the same will also be stored in the knowledge corpus in activity database 132.

In an embodiment, movement recommendation program 101 receives information on the user's movements while performing an activity from user device 110 or sensor 160 and stores this information in activity database 132. For example, user A is wearing an augmented reality headset and lifts a box with their hands from the floor to a table. Here, movement recommendation program 101 receives information on the user's movement of lifting a box with their hands and stores this information in activity database 132. In another example, activity database 132 includes information on the movements or ordered steps that a user needs to perform to complete a particular step or activity. For example, if a user opens a box, takes a shirt out of the box, then puts the shirt on a hanger, movement recommendation program 101 stores the movements detected during these steps and the particular order of the movements in activity database 132. In an embodiment, activity database includes data of the user, such as height, weight, amount of weight a user can carry, etc.

In an embodiment, activity movement guidance policies 134 include a dynamic set of rules for determining directional recommendations based on one or more of the users movement and the desired or optimal movement for performing a particular step or activity, information included in activity database 132, and external environment factors. In an embodiment, external factors can include data of the user, such as height and weight. For example, a user with shorter arms may need to raise their arms higher or at a higher degree than a user with longer arms. Other external factors can include weather and temperature. For example, for an outdoor activity such as weeding plants, a user may complete the task slower when the temperature is hotter or if there is direct sunlight. In an embodiment, the activity movement guidance policies 134 includes information describing different decision-making actions movement recommendation program 101 should perform. In an embodiment, movement recommendation program 101 performs a decision-making action which depends on one or more of: the degree of deviation from the particular current user movement and desired or optimal movement for performing a particular step or activity, information included in activity database 132, and the surrounding environment in which the user is performing a particular step or activity. In an embodiment, movement recommendation program 101 further selects a policy from activity movement guidance policies 134 based on the type of activity being performed. For example, movement recommendation program 101 selects a policy from activity movement guidance policies 134 for the activity of painting a wall based on the degree of deviation from the particular current user movement of painting a wall and the desired or optimal movement of painting a wall. In an embodiment, movement recommendation program 101 accesses information in activity database 132 to determine the desired or optimal movement for performing a particular step or activity.

In an embodiment, AR device 150 an augmented reality headset or other augmented reality device capable of displaying real world and augmented reality objects. In an embodiment, AR device 150 is an IoT enabled system which can include a wearable device, head mounted AR glass, cap, electronic cloth based dress, shoes etc. IoT enabled devices are generating events when any criteria or condition is met. For example, if more than one AR device or sensor is connected to network 140 and collecting information, multiple events are generated as an outcome of different conditions becoming true. In an embodiment, various IoT devices can be involved, in which some of the IoT devices can be wearable devices and some IoT devices can be IoT devices located external to an individual. In an embodiment, AR device 150 tracks the particular steps or activity that is being performed and the movement for each step or activity. For example, AR device 150 tracks the activity of arranging books on a shelf or jogging. In an embodiment, network computing environment 100 includes multiple AR devices 150.

In an embodiment, movement recommendation program 101 receives information from AR device 150 and sensor 160 to determine information on the users movement and activity. In an embodiment, sensor 160 may be installed on AR device 150 and captures different types of data from the activity being performed, and movement recommendation program 101 further identifies the sequence of the steps of the activity based on the data captured via sensor 160. In an embodiment, movement recommendation program 101 further identifies whether a step is being incorrectly performed or deviates beyond a predetermined threshold from an optimal performance of the step. In an embodiment, the optimal performance is the optimal movement from the historical reference activity. In an embodiment, movement recommendation program 101 receives information from AR device 150 and/or sensor 160, and accordingly based on analysis of the IoT feeds, type of activity will be identified. In an embodiment, movement recommendation program 101 tracks the sequence of performing the activities, in this case the time stamp of the IoT signals or movement will be captured.

In an embodiment, sensor 160 is a wearable sensor. For example, sensor 160 is a robotic arm. In an embodiment, network 140 includes multiple sensors 160. In an embodiment, sensor 160 is capable of collecting information about the activity. In an embodiment, sensor 160 collects information on the direction, speed, or velocity of movement of the user or objects associated with an activity. In an embodiment, sensor 160 is located on one or more objects associated with the activity. For example, if the activity is unboxing cups from a box, a sensor is located on a cup or on the box. In an embodiment, movement recommendation program 101 utilizes information captured from sensor 160 to determine the activity being performed or movement of the user. For example, movement recommendation program 101 receives sensor data indicating that the object is moving to the right at 1 mph.

In an embodiment, user wears AR glasses, or AR device 150. In an embodiment, there are multiple AR devices 150 or other wearable AR devices. In an embodiment, while the activity is being performed, the user can also use various other IoT devices in the users proximity. In an embodiment, there are multiple sensors 160. In an embodiment, sensor 160 is a wearable sensor.

In an embodiment, movement recommendation program 101 determines the activity being performed based on user input. For example, movement recommendation program 101 receives user input including information that the activity being performed by the user is building a desk. In an embodiment, movement recommendation program 101 determines the activity based, at least in part, on the movements and steps taken by a user. For example, movement recommendation program 101 determines the user is performing the same movement and movements in the same order or steps to a previously identified activity. In an embodiment, movement recommendation program 101 determines one or more steps for an activity based on historical data associated with similarly performed activities.

In an embodiment, movement recommendation program 101 compares the movement and steps taken by the user to previous or predetermined movements and steps in activity database 132 to determine the current activity or steps of the user. In an embodiment, movement recommendation program 101 determines the activity based, at least in part, on the objects determined in the users field of view. For example, motion and object detection module 122 determines there are multiple planting pots, a bag of soil, a bag of seeds, and a garden hose in the users field of view. Here, movement recommendation program 101 further determines the user is planting seeds in planting pots.

In an embodiment, movement recommendation program 101 compares the reference activity with the current activity to determine a degree of deviation between the current activity and the reference activity. For example, movement recommendation program 101 compares the reference activity of fragile objects with the current activity of unboxing fragile glassware and determines a low deviation between the current activity and the reference activity of fragile objects. In an embodiment, movement recommendation program 101 determines whether the degree of deviation between the current activity and the reference activity is within a permitted range of deviation. For example, movement recommendation program 101 determines the predetermined range of deviation is low and is 5% or lower and further determines whether the degree of deviation between the current activity and the reference activity is 5% or lower. In an embodiment, movement recommendation program 101 determines the permittable range of deviation for a particular step or activity. For example, one type of activity may have a higher deviation range than another activity. For example, if the activity is unwrapping delicate items from a box and bubble wrap, movement recommendation program 101 determines the movement deviation range is low to ensure the delicate items do not break. Here, movement recommendation program 101 determines the movement deviation range is within 5% of the movement from the reference activity to the user's current movement. In another example, movement recommendation program 101 determines the reference movement is for the user to raise their hand holding the object up 10 inches from the block and the user is currently holding the object up 8 inches from the box. In this example, movement recommendation program 101 determines the user is 2 inches away or at a 20% deviation from the reference movement.

In an embodiment, movement recommendation program 101 compares movements of the individual while performing the current activity to corresponding movements in a reference activity. In an embodiment, corresponding movement is the movement the user is doing at a current moment in time or step of an activity. For example, movement recommendation program 101 compares movements of the individual while performing the current activity at step 2 to corresponding movements in a reference activity at step 2. In another example, movement recommendation program 101 compares movements of the individual while performing the current activity at two minutes after starting the activity to corresponding movements in a reference activity at two minutes after starting the activity.

In an embodiment, movement recommendation program 101 determines whether the degree of deviation is above a predetermined threshold. For example, movement recommendation program 101 determines the reference movement is for the user to raise their hand holding the object up 10 inches from the block and the user is currently holding the object up 8 inches from the box. In this example, movement recommendation program 101 determines the user is 2 inches away or at a 20% deviation from the reference movement. Here, movement recommendation program 101 determines the predetermined threshold is a 10% deviation from the reference movement and that the deviation is more than the predetermined threshold.

In an embodiment, movement recommendation program 101 determines a performance level of the user's movement. In an embodiment, the performance level is a score or category associated with a predetermined threshold (e.g., number, score). In an embodiment, the performance level is based, at least in part, on the deviation of the users movement from the reference movement. For example, movement recommendation program 101 determines the reference movement is for the user to raise their hand holding the object up 10 inches from the block and the user is currently holding the object up 9 inches from the box. In this example, movement recommendation program 101 determines the user is 1 inch away or at a 10% deviation from the reference movement. Here, movement recommendation program 101 determines the predetermined threshold is a 10% deviation from the reference movement and gives it a performance level of a 9 out of 10. In an embodiment, movement recommendation program 101 determines a performance level based on if the users movement deviates from the reference movement above a predetermined threshold. For example, if movement recommendation program 101 determines the predetermined threshold is 10% and the users current movement deviation is 25%, movement recommendation program 101 determines a performance level based on the users movement deviating from the reference movement above a predetermined threshold. In this example, movement recommendation program 101 determines the performance level is "requires improvement."

In an embodiment, movement recommendation program 101 generates a directional guidance recommendation. In an embodiment, a direction guidance recommendation includes guidance for performing a step or activity to minimize the deviation of the user's current movement to the reference movement. For example, if movement recommendation program 101 determines the user's movement of holding a glass at a 45 degree angle is above the predetermined deviation threshold of 30 degrees, movement recommendation program 101 generates a directional guidance recommendation for the user to hold the class more upright and at a 30 degree angle. In an embodiment, movement recommendation program 101 utilizes a GAN to generate a visual directional guidance recommendation. In an embodiment, movement recommendation program 101 utilizes a GAN to generate a visual directional guidance recommendation based, at least in part, on the activity and a comparative analysis of the users current movement and the reference movement. In an embodiment, the generated GAN directional guidance recommendation is a textual or pictorial representation of the movement recommendation. For example, if the recommendation is for the user to hold the object in their hand and move the object to the left, the generated GAN directional guidance recommendation is of a picture of the user moving the object in their hand to the left or an arrow pointing to the left.

In an embodiment, movement recommendation program 101 displays the directional guidance recommendation to the user. In an embodiment, movement recommendation program 101 displays the direction guidance recommendation as an augmented reality object in the AR field of view of the user.

In an embodiment, movement recommendation program 101 determines a baseline for future activities. In an embodiment, a baseline can include the baseline movement for an activity. For example, movement recommendation program 101 determines a baseline for future activities based on historically captured activities. In an embodiment, a baseline is a baseline level of performance for an activity or step. In an embodiment, movement recommendation program 101 determines the historically captured activity as preference activity. For example, movement recommendation program 101 determines one or more reference movements for each activity or step. Further, movement recommendation program 101 determines a predetermined deviation threshold from the reference movement for the activity.

In an embodiment, the users selects or indicates the activity being performed. For example, movement recommendation program 101 accesses activity database 132 and displays one or more activities on user device 110. In an embodiment, movement recommendation program 101 receives user input of the activity. In an embodiment, movement recommendation program 101 provides one or more activities or steps to the user. For example, movement recommendation program 101 displays text of the activity or step in AR device 150. In an embodiment, an activity has multiple referred activities. In these embodiments, different steps of the current activity will be referred with respective steps of referred activities. In an embodiment, movement recommendation program 101 identifies the data from AR device 150 or sensor 160 from the referred activities and the activity steps. In an embodiment, movement recommendation program 101 determines or identifies which AR device 150 or sensor 160 devices will be involved to perform the activity. In an embodiment, movement recommendation program 101 identifies AR device 150 or sensor 160 devices are required to perform the activity and will be identifying in the user's surroundings. In an embodiment, movement recommendation program 101 receives information from AR device 150 or sensor 160. In an embodiment, movement recommendation program 101 receives information from AR device 150 or sensor 160 on how the user is performing the activity, and AR device 150 or sensor 160 will be generating signals. In an embodiment, movement recommendation program 101 compares the current information from AR device 150 or sensor 160 on how the user is performing the activity and the preference movement for the activity or steps. In an embodiment, movement recommendation program 101 determines the deviation between how the user is performing the activity from the preference movement. In an embodiment, movement recommendation program 101 determines the deviation between how the user is performing the activity from the preference movement is above a predetermined threshold. In an embodiment, movement recommendation program 101 utilizes a GAN for a baseline remediation. In an embodiment, movement recommendation program 101 utilizes a GAN to create appropriate image sequence. For example, movement recommendation program 101 utilizes a GAN to create a pictorial image of a directional recommendation to mediate the user's movement to the preference movement. In an embodiment, movement recommendation program 101 appropriate notification or displaying of the pictorial image sequence will be shown in the AR glass, so that the user can perform the activity aligned with the referred activity.

In an embodiment, movement recommendation program 101 determines a current activity of an individual. In an embodiment, movement recommendation program 101 compares movements of the individual while performing the current activity to corresponding movements in a reference activity. In an embodiment, movement recommendation program 101 determines whether a performance level of respective movements of the individual while performing the current activity are within a predetermined performance range associated with the corresponding movements in the reference activity. In an embodiment, responsive to determining that the performance level of at least one movement of the individual while performing the current activity is outside of the predetermined performance range of a corresponding movement included in the reference activity, movement recommendation program 101 generates, via a generative adversarial network (GAN), a directional guidance recommendation based, at least in part, on: a comparative analysis of the at least one movement of the individual while performing the current activity and the corresponding movement included in the reference activity, and a degree of deviation between the performance level of the at least one movement of the individual and an optimal performance level of the corresponding movement included in the reference activity. In an embodiment, the generated GAN directional guidance comprises a visual depiction correcting the at least one movement that is outside of the predetermined performance range of the corresponding movement included in the reference activity. In an embodiment, movement recommendation program 101 displays the generated directional guidance recommendation to the individual while the individual is performing the current activity.

Figure 2:
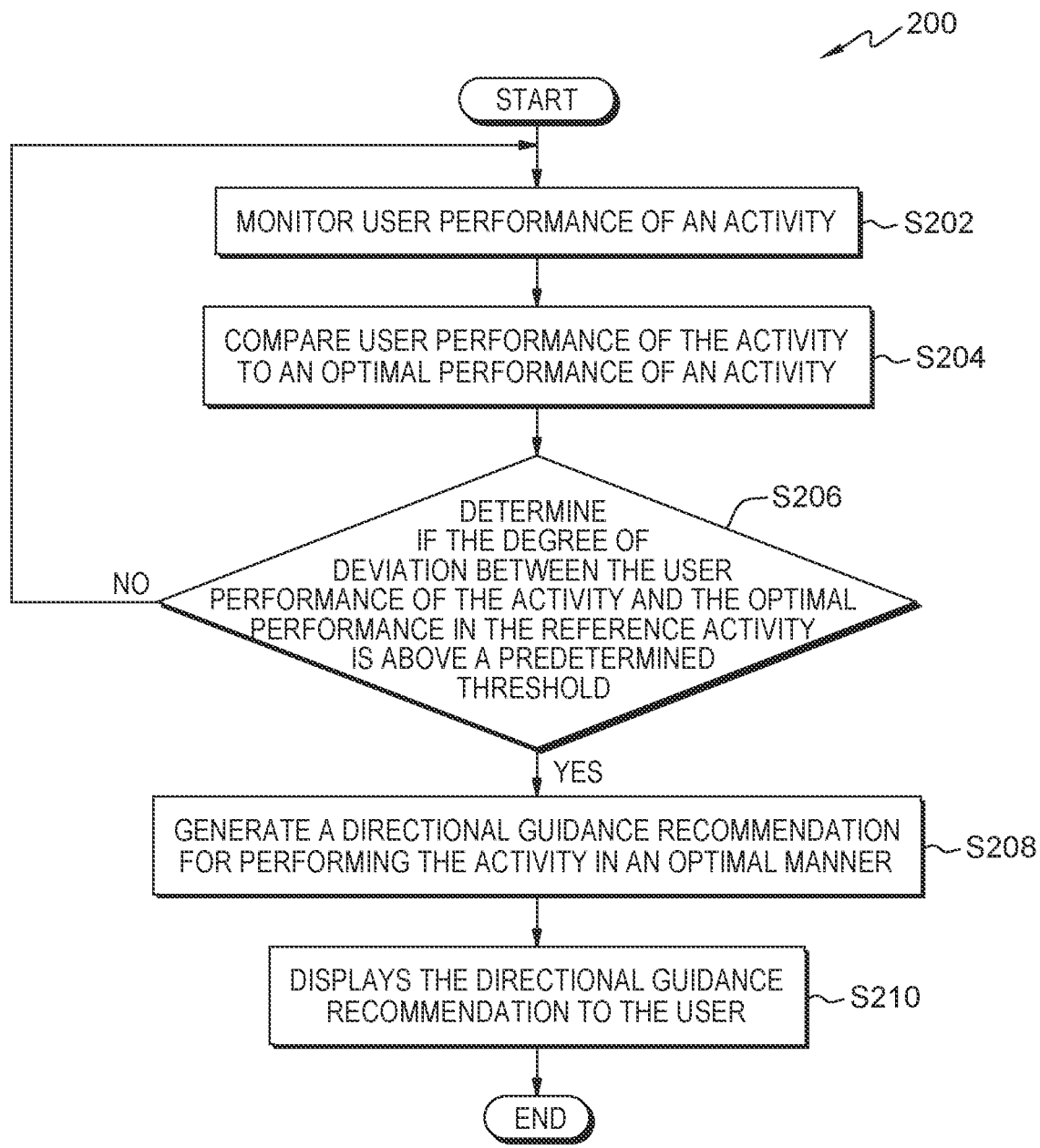
FIG. 2 is a flow chart diagram depicting operational steps for movement recommendation program 101, generally designated 200, in accordance with at least one embodiment of the present invention.

FIG. 2 is a flow chart diagram depicting operational steps for movement recommendation program 101, generally designated 200, in accordance with at least one embodiment of the present invention. FIG. 2 provides only an illustration of one implementation and does not imply any limitations with regard to the environments in which different embodiments may be implemented. Many modifications to the depicted environment may be made by those skilled in the art without departing from the scope of the invention as recited by the claims.

At step S202, movement recommendation program 101 monitors user performance of an activity. In an embodiment, movement recommendation program 101 monitors the user performance of an activity based on information received from AR device 150 and sensor 160 while a user is performing an activity.

At step S204, movement recommendation program 101 compares the user performance of the activity to an optimal performance of an activity. In an embodiment, movement recommendation program 101 compares the user performance of the activity to a historical reference activity. For example, movement recommendation program 101 compares the angle of the users arm holding an object to the angle of holding an object in the historical reference activity. In an embodiment, movement recommendation program 101 determines the degree of deviation based, at least in part, on the current activity. For example, movement recommendation program 101 determines the current activity is handling fragile objects and the range of deviation is low. In an embodiment, comparing the user performance with the optimal performance includes determining a degree of deviation between the user performance of the current activity and the optimal performance in the reference activity. For example, movement recommendation program 101 compares the user performance with the optimal performance to determine the degree of deviation to be 6%. Meaning, the users current performance movement is within 6% of the optimal performance. In an embodiment, movement recommendation program 101 determines whether the degree of deviation between the current activity and the reference activity is within a permitted range of deviation. For example, if movement recommendation program 101 determines the degree of deviation between the current activity and the reference activity is 6% but the range of deviation is 5%, movement recommendation program 101 determines the deviation between the current activity and the reference activity is not within the permitted range of deviation.

At decision step S206, movement recommendation program 101 determines if the degree of deviation between the user performance of the activity and the optimal performance in the reference activity is above a predetermined threshold. If movement recommendation program 101 determines that the degree of deviation between the user performance of the activity and the optimal performance in the reference activity is not above the predetermined threshold (decision step S206 "NO" branch), movement recommendation program 101 returns to step S202. If movement recommendation program 101 determines that the degree of deviation between the user performance of the activity and the optimal performance in the reference activity is above the predetermined threshold (decision step S206 "YES" branch), movement recommendation program 101 proceeds to step S208.

At step S208, responsive to determining that the degree of deviation between the user performance of the activity and the optimal performance in the reference activity is above the predetermined threshold, movement recommendation program 101 generates a directional guidance recommendation for performing the activity in an optimal manner. In an embodiment, movement recommendation program 101 utilizes a GAN to generate a directional guidance recommendation based, at least in part, on the activity being performed and a comparative analysis of the users current movement with an optimal reference movement. In an embodiment, the generated GAN directional guidance recommendation is a textual or pictorial representation of the directional movement recommendation.

At step S210, movement recommendation program 101 displays the directional guidance recommendation to the user. In an embodiment, movement recommendation program 101 displays the directional guidance recommendation to the user via AR device 150.

Figure 3:
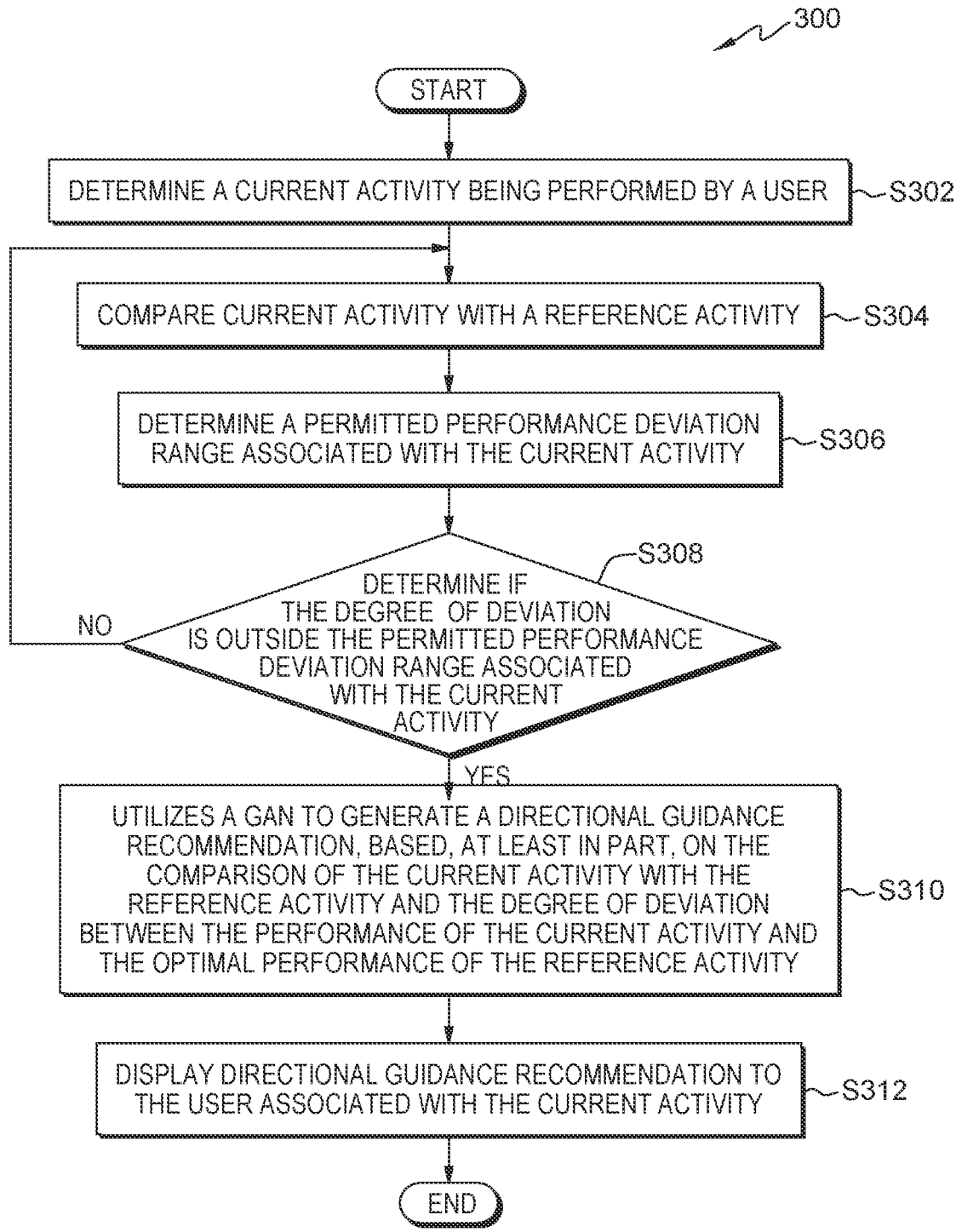
FIG. 3 is a flow chart diagram depicting operational steps for movement recommendation program 101, generally designated 300, in accordance with at least one embodiment of the present invention.

FIG. 3 is a flow chart diagram depicting operational steps for movement recommendation program 101, generally designated 300, in accordance with at least one embodiment of the present invention. FIG. 3 provides only an illustration of one implementation and does not imply any limitations with regard to the environments in which different embodiments may be implemented. Many modifications to the depicted environment may be made by those skilled in the art without departing from the scope of the invention as recited by the claims.

At step S302, movement recommendation program 101 determines a current activity being performed by a user.

At step S304, movement recommendation program 101 compares the current activity with a reference activity. In an embodiment, movement recommendation program 101 identifies one or more steps in the reference activity or current activity. For example, if the current activity is planting sunflowers and the reference activity is planting plants, movement recommendation program 101 identifies one or more steps for planting plants or planting sunflowers.

At step S306, movement recommendation program 101 determines a permitted performance deviation range associated with the current activity. In an embodiment, the permitted performance deviation range is based, at least in part, on the reference activity.

At decision step S308, movement recommendation program 101 determines if the degree of deviation is outside the permitted performance deviation range associated with the current activity. If movement recommendation program 101 determines that the degree of deviation is not outside the permitted performance deviation range associated with the current activity (decision step S308 "NO" branch), movement recommendation program 101 returns to S304. If movement recommendation program 101 determines that the degree of deviation is outside the permitted performance deviation range associated with the current activity (decision step S308 "YES" branch), movement recommendation program 101 proceeds to step S310.

At step S310, responsive to determining the degree of deviation is outside the permitted performance deviation range associated with the current activity, movement recommendation program 101 utilizes a GAN to generate a directional guidance recommendation, based, at least in part, on the comparison of the current activity with the reference activity and the degree of deviation between the performance of the current activity and the optimal performance of the reference activity. In an embodiment, movement recommendation program 101 utilizes a GAN to regenerate one or more objects or guidance recommendations. For example, GAN regenerates an object depicting the guidance recommendation, such as holding the object higher or lower than the individual is currently holding the object.

At step S312, movement recommendation program 101 displays the directional guidance recommendation to the user associated with the current activity. In an embodiment, movement recommendation program 101 displays the directional guidance recommendation in the field of view of the AR device. For example, if a GAN generates a directional guidance recommendation depicting the users arm raising an object upward, movement recommendation program 101 displays the directional guidance recommendation depicting the users arm raising an object upward recommendation in the field of view of the AR device.

FIG. 4 is a block diagram depicting components of a computing device, generally designated 400, suitable for movement recommendation program 101 in accordance with at least one embodiment of the invention. Computing device 400 includes one or more processor(s) 404 (including one or more computer processors), communications fabric 402, memory 406 including, RAM 416 and cache 418, persistent storage 408, which further includes movement recommendation program 101, communications unit 412, I/O interface(s) 414, display 422, and external device(s) 420. It should be appreciated that FIG. 4 provides only an illustration of one embodiment and does not imply any limitations with regard to the environments in which different embodiments may be implemented. Many modifications to the depicted environment may be made.

As depicted, computing device 400 operates over communications fabric 402, which provides communications between computer processor(s) 404, memory 406, persistent storage 408, communications unit 412, and input/output (I/O) interface(s) 414. Communications fabric 402 can be implemented with any architecture suitable for passing data or control information between processor(s) 404 (e.g., microprocessors, communications processors, and network processors), memory 406, external device(s) 420, and any other hardware components within a system. For example, communications fabric 402 can be implemented with one or more buses.

Memory 406 and persistent storage 408 are computer readable storage media. In the depicted embodiment, memory 406 includes random-access memory (RAM) 416 and cache 418. In general, memory 406 can include any suitable volatile or non-volatile computer readable storage media.

Program instructions for movement recommendation program 101 can be stored in persistent storage 408, or more generally, any computer readable storage media, for execution by one or more of the respective computer processor(s) 404 via one or more memories of memory 406. Persistent storage 408 can be a magnetic hard disk drive, a solid-state disk drive, a semiconductor storage device, read-only memory (ROM), electronically erasable programmable read-only memory (EEPROM), flash memory, or any other computer readable storage media that is capable of storing program instructions or digital information.

Media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 412, in these examples, provides for communications with other data processing systems or devices. In these examples, communications unit 412 can include one or more network interface cards. Communications unit 412 may provide communications through the use of either or both physical and wireless communications links. In the context of some embodiments of the present invention, the source of the various input data may be physically remote to computing device 400 such that the input data may be received, and the output similarly transmitted via communications unit 412.

I/O interface(s) 414 allows for input and output of data with other devices that may operate in conjunction with computing device 400. For example, I/O interface(s) 414 may provide a connection to external device(s) 420, which may be as a keyboard, keypad, a touch screen, or other suitable input devices. External device(s) 420 can also include portable computer readable storage media, for example thumb drives, portable optical or magnetic disks, and memory cards. Software and data used to practice embodiments of the present invention can be stored on such portable computer readable storage media and may be loaded onto persistent storage 408 via I/O interface(s) 414. I/O interface(s) 414 also can similarly connect to display 422. Display 422 provides a mechanism to display data to a user and may be, for example, a computer monitor.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

FIG. 5 is a block diagram depicting a cloud computing environment 50 in accordance with at least one embodiment of the present invention. Cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
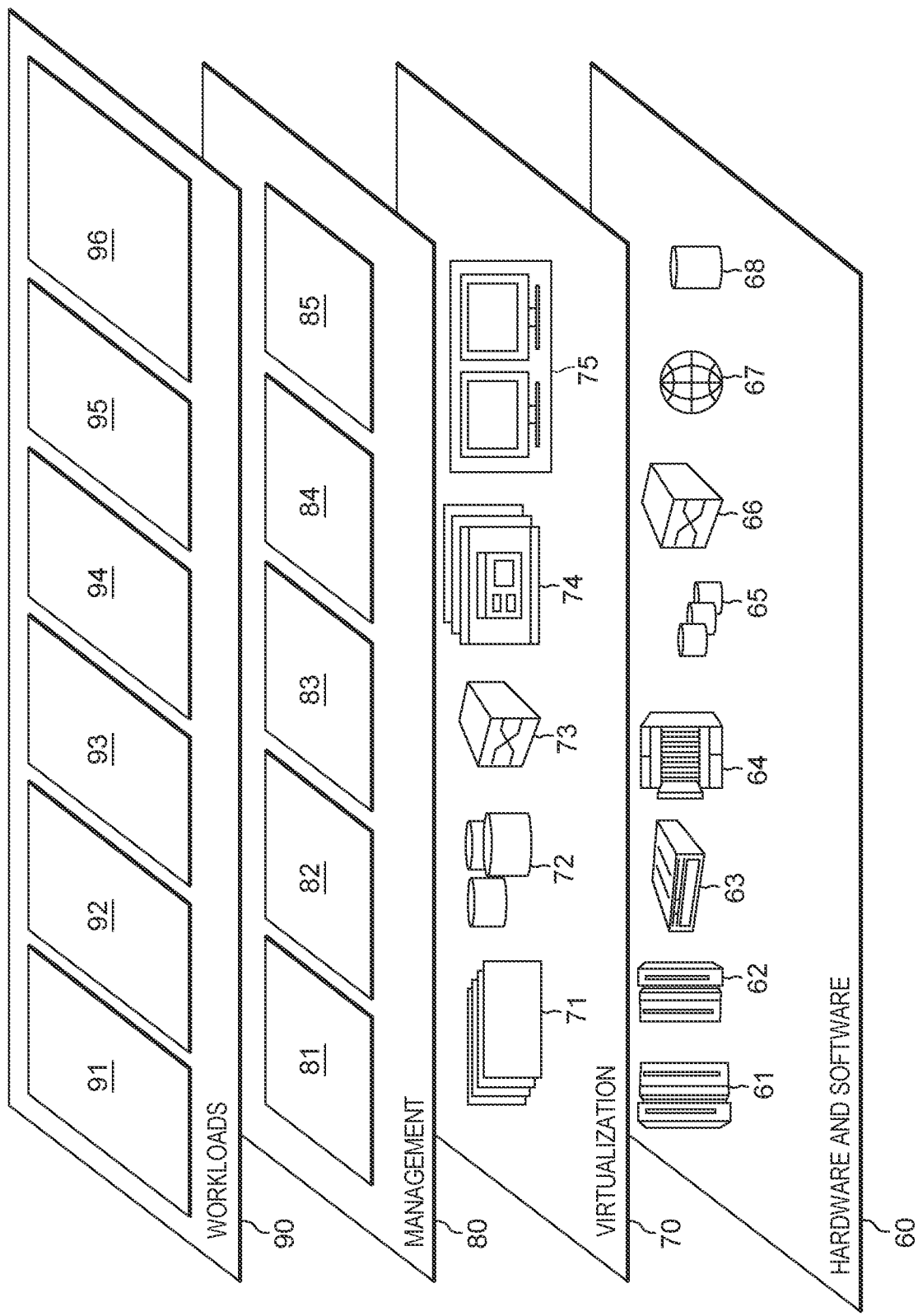
FIG. 6 is block diagram depicting a set of functional abstraction model layers provided by cloud computing environment 50 depicted in FIG. 5 in accordance with at least one embodiment of the present invention.

FIG. 6 is block diagram depicting a set of functional abstraction model layers provided by cloud computing environment 50 depicted in FIG. 5 in accordance with at least one embodiment of the present invention. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and directional recommendation generation 96.

What is claimed is:

1. A computer-implemented method, the computer-implemented method comprising:
    determining a current activity of an individual;
    comparing movements of the individual while performing the current activity to corresponding movements in a reference activity;
    determining whether a performance level of respective movements of the individual while performing the current activity are within a predetermined performance range associated with the corresponding movements in the reference activity; and
    responsive to determining that the performance level of at least one movement of the individual while performing the current activity is outside of the predetermined performance range of a corresponding movement included in the reference activity, generating, via a generative adversarial network (GAN), a directional guidance recommendation based, at least in part, on:
        a comparative analysis of the at least one movement of the individual while performing the current activity and the corresponding movement included in the reference activity, and a degree of deviation between the performance level of the at least one movement of the individual and an optimal performance level of the corresponding movement included in the reference activity; and
        displaying the generated directional guidance recommendation to the individual while the individual is performing the current activity.

2. The computer-implemented method of claim 1, wherein the directional guidance recommendation comprises guidance for performing the individuals current activity to minimize the degree of deviation of the individuals current movement to the optimal performance level of the corresponding movement included in the reference activity.

3. The computer-implemented method of claim 1, further comprising:
  identifying one or more steps included in the reference activity;
  determining one or more steps associated with the movements of the individual while performing the current activity; and
  determining a degree of deviation between each of the one or more steps associated with respective movements of the individual while performing the current activity and respective optimal performance levels of corresponding movements included in the reference activity.

4. The computer-implemented method of claim 1, wherein comparing movements of the individual while performing the current activity to corresponding movements in a reference activity further comprises:
  determining a baseline for a future activity based, at least in part, on historically captured activities.

5. The computer-implemented method of claim 1, wherein the predetermined threshold associated with the individuals current activity is based, at least in part, on the reference activity.

6. The computer-implemented method of claim 1, wherein determining the individuals current activity is based, at least in part, on the movements of the individual.

7. The computer-implemented method of claim 1, wherein the directional guidance recommendation generated via the GAN further comprises a visual depiction correcting the at least one movement that is outside of the predetermined performance range of the corresponding movement included in the reference activity.

8. A computer program product, the computer program product comprising one or more computer readable storage media and program instructions stored on the one or more computer readable storage media, the program instructions including instructions to:
  determine a current activity of an individual;
  compare movements of the individual while performing the current activity to movements associated with a reference activity;
  determine whether a performance level of respective movements of the individual while performing the current activity are within a predetermined performance range associated with corresponding movements in the reference activity; and
  responsive to determining that the performance level of at least one movement of the individual while performing the current activity is outside of the predetermined performance range of a corresponding movement included in the reference activity, generate, via a generative adversarial network (GAN), a directional guidance recommendation based, at least in part, on:
    a comparative analysis of the at least one movement of the individual while performing the current activity and the corresponding movement included in the reference activity, and a degree of deviation between the performance level of the at least one movement of the individual and an optimal performance level of the corresponding movement included in the reference activity; and
  display the generated directional guidance recommendation to the individual while the individual is performing the current activity.

9. The computer program product of claim 8, wherein the directional guidance recommendation comprises guidance for performing the individuals current activity to minimize the degree of deviation of the individuals current movement to the optimal performance level of the corresponding movement included in the reference activity.

10. The computer program product of claim 8, further comprising instructions to:
  identify one or more steps included in the reference activity;
  determine one or more steps associated with the movements of the individual while performing the current activity; and
  determine a degree of deviation between each of the one or more steps associated with respective movements of the individual while performing the current activity and respective optimal performance levels of corresponding movements included in the reference activity.

11. The computer program product of claim 8, wherein the instructions to compare movements of the individual while performing the current activity to corresponding movements in a reference activity further comprises instructions to:
  determine a baseline for a future activity based, at least in part, on historically captured activities.

12. The computer program product of claim 8, wherein the predetermined threshold associated with the individuals current activity is based, at least in part, on the reference activity.

13. The computer program product of claim 8, wherein determining the individuals current activity is based, at least in part, on the movements of the individual.

14. The computer program product of claim 8, wherein the directional guidance recommendation generated via the GAN further comprises a visual depiction correcting the at least one movement that is outside of the predetermined performance range of the corresponding movement included in the reference activity.

15. A computer system comprising:
  one or more computer processors;
  one or more computer readable storage media;
  computer program instructions;
  the computer program instructions being stored on the one or more computer readable storage media for execution by the one or more computer processors; and
  the computer program instructions including instructions to:
    determine a current activity of an individual;
    compare movements of the individual while performing the current activity to movements associated with a reference activity;
    determine whether a performance level of respective movements of the individual while performing the current activity are within a predetermined performance range associated with corresponding movements in the reference activity; and
    responsive to determining that the performance level of at least one movement of the individual while performing the current activity is outside of the predetermined performance range of a corresponding movement included in the reference activity, generate, via a generative adversarial network (GAN), a directional guidance recommendation based, at least in part, on:
      a comparative analysis of the at least one movement of the individual while performing the current activity and the corresponding movement included in the reference activity, and a degree of deviation between the performance level of the at least one movement of the individual and an optimal performance level of the corresponding movement included in the reference activity; and display the generated directional guidance recommendation to the individual while the individual is performing the current activity.

16. The computer system of claim 15, wherein the directional guidance recommendation comprises guidance for performing the individuals current activity to minimize the degree of deviation of the individuals current movement to the optimal performance level of the corresponding movement included in the reference activity.

17. The computer system of claim 15, further comprising instructions to:
identify one or more steps included in the reference activity;
determine one or more steps associated with the movements of the individual while performing the current activity; and
determine a degree of deviation between each of the one or more steps associated with respective movements of the individual while performing the current activity and respective optimal performance levels of corresponding movements included in the reference activity.

18. The computer system of claim 15, wherein the instructions to compare movements of the individual while performing the current activity to corresponding movements in a reference activity further comprises instructions to:
determine a baseline for a future activity based, at least in part, on historically captured activities.

19. The computer system of claim 15, wherein the predetermined threshold associated with the individuals current activity is based, at least in part, on the reference activity.

20. The computer system of claim 15, wherein the directional guidance recommendation generated via the GAN further comprises a visual depiction correcting the at least one movement that is outside of the predetermined performance range of the corresponding movement included in the reference activity.

* * * * *